United States Patent [19]
Michael et al.

[11] Patent Number: 5,550,763
[45] Date of Patent: Aug. 27, 1996

[54] USING CONE SHAPED SEARCH MODELS TO LOCATE BALL BONDS ON WIRE BONDED DEVICES

[76] Inventors: David J. Michael, 124 Cabot St., Newton, Mass. 02158; Juha Koljonen, 65 Powers St., Needham, Mass. 02192; Arman Garakani, 12 Chauncey St. Apartment 2, Cambridge, Mass. 02138

[21] Appl. No.: 236,211

[22] Filed: May 2, 1994

[51] Int. Cl.⁶ ........................... G01B 11/24; G01N 21/86
[52] U.S. Cl. ..................... 364/582; 364/491; 382/145; 382/169; 382/199; 348/87
[58] Field of Search ............................ 228/102; 356/394, 356/237, 376; 348/131, 126, 87; 364/491, 492, 582, 560; 382/8, 25, 48, 126, 145, 169, 199

[56] References Cited

U.S. PATENT DOCUMENTS

| | | |
|---|---|---|
| 4,240,750 | 12/1980 | Kuntz et al. . |
| 4,347,964 | 9/1982 | Takasugi et al. . |
| 4,421',410 | 12/1983 | Karashi . |
| 4,439,010 | 3/1984 | Doty . |
| 4,441,248 | 8/1984 | Sherman et al. . |
| 4,799,175 | 1/1989 | Sano et al. . |
| 5,119,436 | 6/1992 | Holdgrafer ................... 382/8 |
| 5,138,180 | 8/1992 | Yamanaka . |
| 5,156,319 | 10/1992 | Shibasaka et al. . |
| 5,170,006 | 12/1992 | Miyahara . |
| 5,225,891 | 6/1993 | Choumei . |

*Primary Examiner*—Emanuel T. Voeltz
*Assistant Examiner*—Kamini S. Shah

[57] ABSTRACT

Method and apparatus for automatically locating the center of a ball bond of a wire to a lead frame and semiconductor chip or similar device; analyzing the optically sensed images; a bonding mechanism; and a host controller connected to the bonding mechanism, the movable platform. The present invention constructs a synthetic flattened cone model using a center radius, and monotonically increasing slope values to generate a model having a variation in grey levels, and inner and outer radii that will encompass expected size variations in a ball bond; sets a threshold for acceptable normalized correlation search results; acquires a digitized image of the bond, including a nominal location for the bond; conducts a normalized correlation search of the digitized image at the bond location, using the flattened synthetic cone model; and indicates the presence and location of the expected circular object as the location having the largest coefficient which exceeds a threshold.

8 Claims, 9 Drawing Sheets

FIG. 9

```
grey(x,y) is the grey level of the model or NM for not in the
model.
top is the top of the model (maybe 0)
left is the left of the model (maybe 0)
right is the right side of the model (maybe model width)
bottom is the bottom of the model (maybe model height)
centerx is (left + right)/2
centery is (top + bottom)/2
rinner is the inner circle radius
router is the outer circle radius
slope is 254 / (router - rinner)

Here is the pseudocode that produces the cone model

Iterate through each pixel in the model image
for (x = left; x <= right; x++)
        for (y = top; y<= bottom; y++)
First find the radius at that location
            radius = sqrt( (x - centerx)^2 + (y - centery)^2 );
Set the grey level to the plateau value if the radius is less then
rinner
            if (radius < rinner)
                    then grey(x, y) = 254;
Set the grey level to the location on the slope if it is less then
router
            else if (radius < router)
                    then grey(x, y) slope X (router - radius);
Otherwise, set the pixel to not-in-the-model
            else grey(x, y) = NM;
```

FIG. 10

```
/* This is the actual code to create the cone model */
/* size = (inner_radius + outer_radius) / 2;         */
/* slop = outer_radius - size;                       */
/* Model_Care_Image      = c3o_make_sm (size, slop, 0, 254);            */
/* Model_Dont_Care_Image = c3o_make_sm (size + (slop << 8), 0, 255,0); */ unsigned char c3o_idisk (x, y, rad, dith, fg, bg)
int x, y;
int rad;      /* 32.8 */
int dith;     /* int */
int fg, bg;
{ int dist, mid;
  int  xf = x << 8, yf = y << 8;

mid = (fg + bg) / 2;
  dist = cia_sqrt (xf * xf + yf * yf);

if (dist - rad >= dith << 8) return bg;
  else
    if (dist - rad <= -dith << 8 ) return fg;
    else
      return (unsigned char) (((mid) * ((dist - rad) / dith)>> 8) + mid);
} cip_buffer* c3o_make_disk (model, rad, dith, fg, bg)
cip_buffer *model;
int rad, dith;
int fg, bg;
{ int
    xsize = model->width,
    ysize = model->height,
    x0 = xsize / 2,
    y0 = ysize / 2,
    x, y;

for (y = 0; y < ysize; y++)
    for (x = 0; x < xsize; x++)
      model->put (model, x, y, c3o_idisk (x - x0, y - y0, rad, dith, fg, bg));
  return dst;
}
```

USING CONE SHAPED SEARCH MODELS TO LOCATE BALL BONDS ON WIRE BONDED DEVICES

BACKGROUND OF THE INVENTION

The present invention relates generally to semiconductor chip wire bonding devices, and similar bonding apparatus, and particularly to a method and apparatus for locating a ball bond formed on a pad of a semiconductor chip, in order to perform automated optical inspection of wire bonding in such a device.

Semiconductor devices, such as integrated circuit chips, are electrically connected to leads on a lead frame by a process known as wire bonding. The wire bonding operation involves bonding a wire to electrically connect pads residing on a die (semiconductor chip) to a lead in a lead frame. Once the chip and lead frame have been wire bonded, they can be packaged in ceramic or plastic to form an integrated circuit device. A post-process inspection step, commonly called the third optical inspection, typically involves locating the position of all bonds on the device, the wire connections and the wire heights using optical means.

Heretofore the third optical inspection has been accomplished only after the device is completely bonded and sent to a separate machine or operator. In the majority of cases, the inspection is done by a human operator using a microscope. This manual method can be time-consuming and costly.

Separate machines are available to perform this step, but this requires another piece of capital equipment in the production line. Additionally, a post-process inspection machine has a more difficult time locating the bond to perform a successful inspection because all the information about the chip that was available during the bonding operation, such as exact pad and frame positions and information about other detail have been lost.

This is further complicated by the fact that most semiconductor chips have a considerable amount of visual detail (such as the images of the circuits themselves) which must be circumvented in analyzing the post-bond image to find the bonds. In post-process inspections, some of this detail can be mistaken for parts of the bonds.

Automatically locating the center of a ball bond in an image is required to accurately detect the presence or absence of the ball bond on a pad on a semiconductor die; to find the bond's precise location on a pad, and to serve as a principal step in automating the inspection of the quality of a connection to a pad.

Machine vision systems or image processing systems (systems that capture images, digitize them and use a computer to perform image analysis) have been used on wirebonding machines to align devices and guide the machine for correct bonding placement, but have heretofore not been used during the process to locate the bonds formed and inspect them.

Where post process inspections are automated, the visual detail that is unrelated to the bond may be misinterpreted as part of the bond in a post-process inspection, giving rise to erroneous acceptance or rejection rates. Visual imperfections on the pads and leads caused by probe marks, discoloration, or imperfect illumination further complicate these difficulties. These blemishes may be misconstrued as defects in the bonding process, without the information that was available during the bonding operation.

An additional problem encountered in attempting to perform the inspection in-process can be created by the differences caused by bonding itself. Depending on the type of bonding process and equipment used, heating, cooling, movement and other mechanical factors can create alignment problems for images taken before and after the bonding process, thus making it harder to locate the bond. Thus, ball bonds are typically located by hand in a manual inspection procedure, since there are no accepted techniques in the field for automatically locating ball bonds in images.

Using normalized correlation templates is an accepted machine vision technique to find objects in imagery, but with this technique the template is extremely specific to the object at hand and not flexible enough to handle variations in size or shape. Ball bonds, although generally circular or elliptical, are likely to vary significantly in size and shape.

One approach which has been tried involves foregoing any attempt to automatically locate the ball bond after bonding, because of the difficulties mentioned above. In this approach a system would assume that the bonds have been (correctly) placed by the wire bonder machine, as guided by the machine vision system, and the system would use those nominal locations on the semiconductor die as the precise ball bond location. The problem with this approach is that a typical wire bonder machine's inaccuracies in positioning will very frequently cause the later inspection step to fail.

SUMMARY

The present invention generates a synthetic, flattened cone-shaped model to use with a normalized correlation search in order to locate ball bonds on an image of a semiconductor die pad as part of an automatic in process inspection or an automatic post process inspection. According to a preferred embodiment of the present invention, the synthetic flattened cone shaped model is created by selecting a central diameter and a monotonically increasing slope parameter to create a template having an inner diameter no smaller than the smallest expected bond size and an outer diameter no larger than the largest expected ball size. These diameters are chosen by considering the minimum enclosed circle and maximum enclosing circle of the ball bonds that would be observed in a visual inspection system. The inner diameter should be no smaller then the minimum enclosed circle that will be observed and the outer diameter should be no larger then the maximum enclosing circle.

In a preferred embodiment of the present invention, a portion of the resulting model is suppressed such that a wedge or pie-shaped area is created in the general area where the wire should be positioned. Confusion caused by the non-circular shape of the wire is thus reduced for the search process.

The cone shaped search model of the present invention is synthesized by setting the grey value to $$k, |r| < r \text{ inner}$$

$$\text{slope} \times (r \text{ outer} - r) \ \{|r| \geq r \text{ inner}, |r| < r \text{ outer}\}$$

$$\text{where slope} = \frac{k}{(r \text{ outer} - r \text{ inner})}$$

and optionally not defining the template at angles ±b degrees near the incident wire angle, w.

The present invention uses the cone shaped search model as the template for a normalized correlation search that is performed by the vision processor or image processing system after wire bonding has occurred. In a preferred embodiment, the results of the search will indicate the presence, and hence the location, of the ball bond as a peak in the computed correlation. The absence of a peak indicates that the ball bond is not present. From the location coordinates returned by the search, a nominal center of the ball bond is calculated and passed to the system for use in the next inspection steps. It is an object of the present invention that a single flexible normalized correlation template can be created and used to detect all ball bonds on a semiconductor die pad, thus avoiding the requirement of building a special ball bond template for every possible size and shape ball bond. It is a feature of the present invention that the single flattened cone-shaped template is appropriate for locating the position of ball bonds in images even as the bonds vary in radius and circularity.

It is yet another feature that since normalized correlation is used, the system is insensitive to linear changes in illumination in the image.

Another aspect of the present invention is that the single flattened cone-shaped template is appropriate for locating the position of ball bonds in images even as the bonds vary in radius and circularity.

BRIEF DESCRIPTION OF THE DRAWINGS

FIG. 9 contains pseudo code illustrating the invention.

FIG. 10 contains code in the C computer language used in a preferred embodiment to create a cone model.

DETAILED DESCRIPTION OF THE INVENTION

Figure 1:
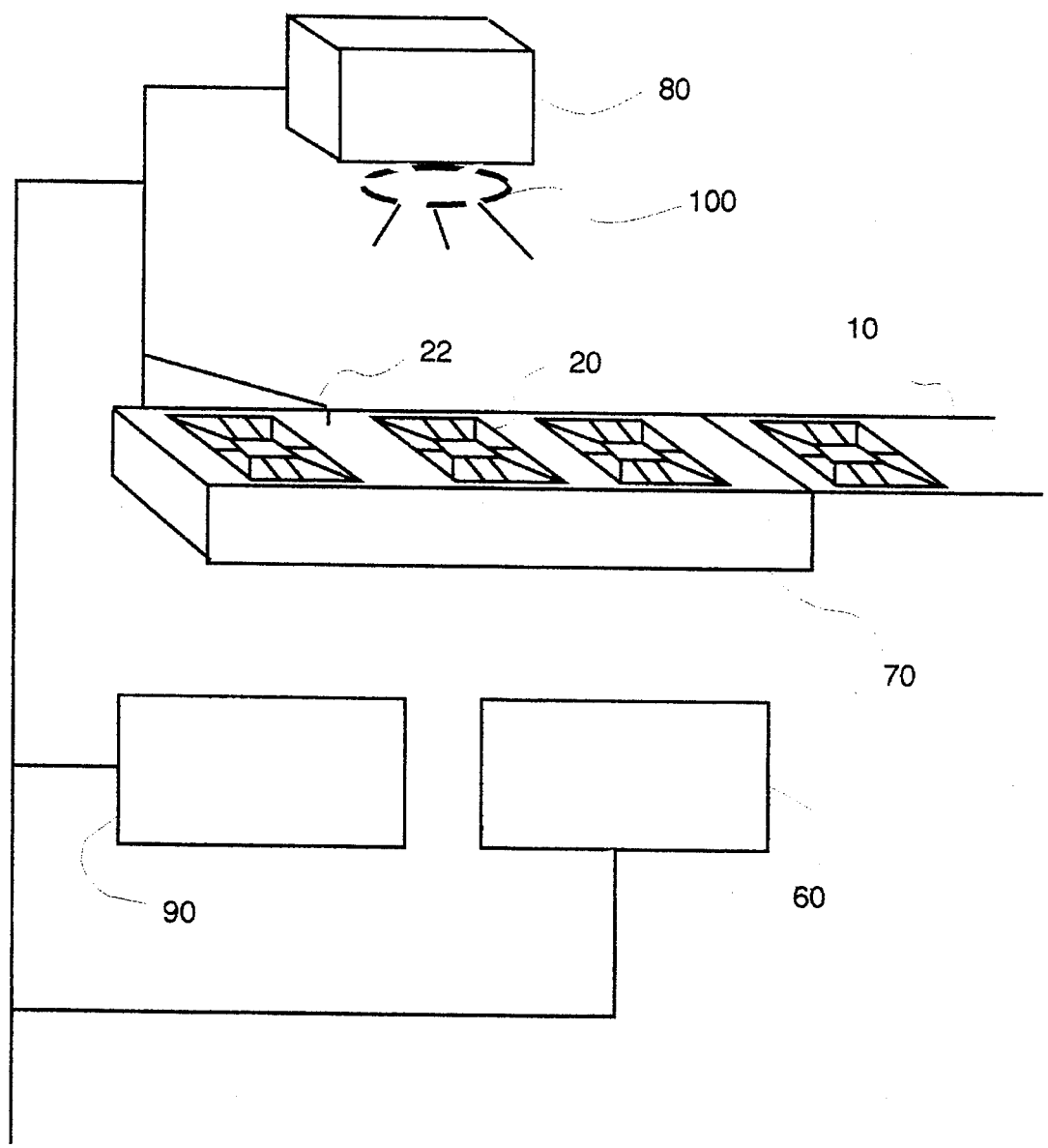
FIG. 1 is an illustration of a system incorporating the present invention.

In FIG. 1, a system incorporating the present invention is shown. The system includes a wire bonding machine having a movable platform such as an X-Y table 70 for holding semiconductor chips 20 situated in a lead frame 10; a video camera 80 or other optical sensing device for generating images, which camera is typically positioned over the target chip and lead frame 10 to be bonded; illumination means 100 for illuminating the chip in a lead frame; an image processor 90 capable of digitizing and analyzing the optically sensed images; bonding mechanism 22; and host controller 60 electronically connected to the bonding 22, the movable platform 70, the camera 80, and the image processor 90.

Figure 2:
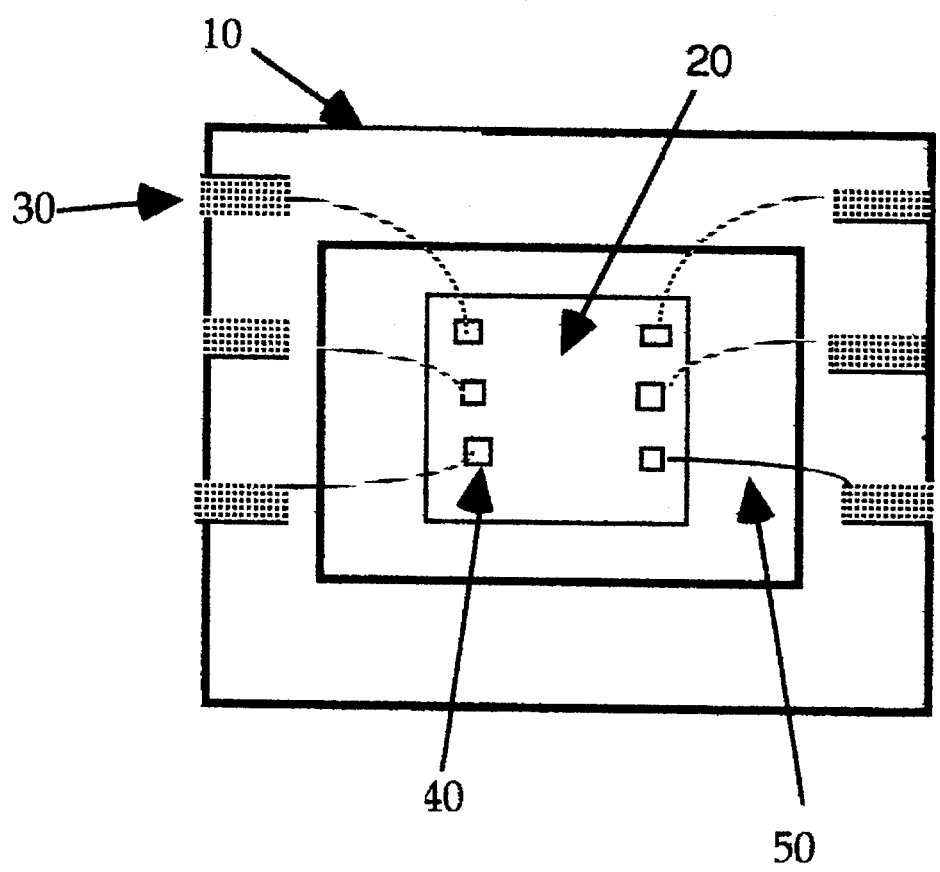
FIG. 2 is a diagrammatic view, taken from above, of a semiconductor chip or die in a lead frame.

FIG. 2 depicts a semiconductor chip 20, in a lead frame 10, having pads 40, and leads 30. The wire bonding process bonds a conductive wire between each pad on the chip 20 and its respective lead 30 on lead frame 10.

Figure 3:
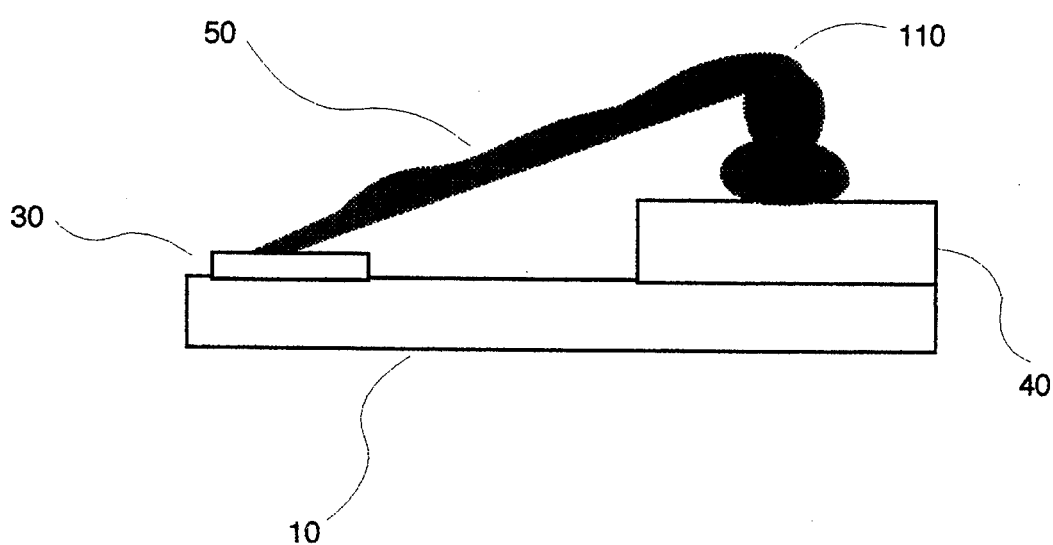
FIG. 3 shows a side view of a bond formed on a pad connected to a lead on a lead frame.

FIG. 3 shows a side view of a ball bond 110, connecting a pad 40 to a lead 30, on a lead frame 10 by a wire 50. In a typical wire bonding device, a wire 50 or filament is extruded by the bonder and deposited on the die pad and extended to the lead frame, where the wire is also affixed, to form an electrical connection.

Figure 3A:
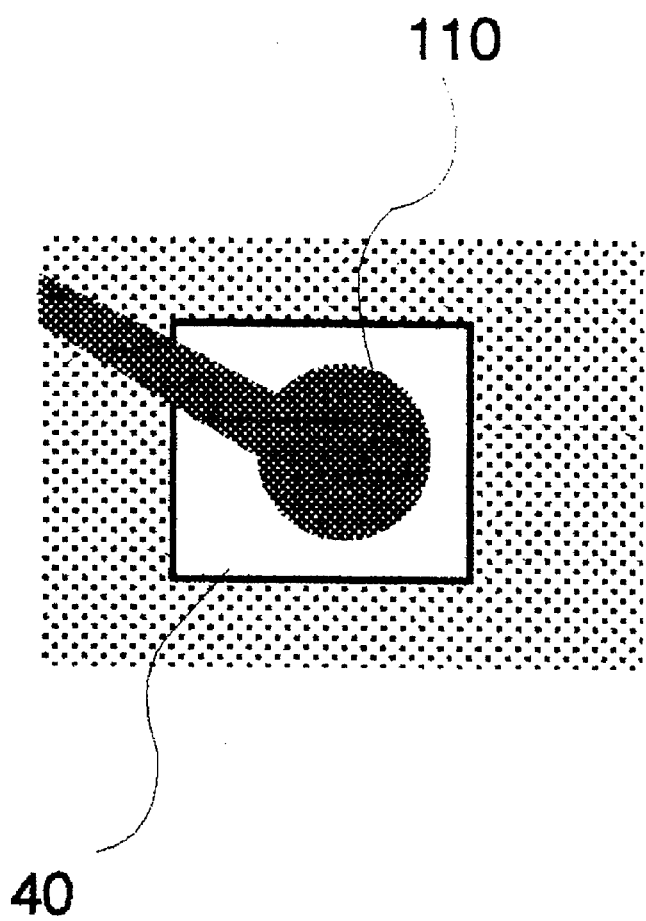
FIG. 3a shows a top view of a bond formed on pad of a semiconductor chip, together with a wire extending from a ball bond.

FIG. 3a shows a top view of a bond formed on a pad 40 of a semiconductor chip 20, together with a wire 50 extending from ball bond 110. In a preferred embodiment of the present invention, an approximate location of a bond 110, on a pad 40, is found using Applicant's Assignee's co-pending applications: Automated Optical Inspection Apparatus filed 06 Oct. 1993, Ser. No. 08/132,532 Attorney Docket No. C93-007 (now abandoned) and the co-pending file wrapper continuation thereof, Automated Optical Inspection Apparatus application Ser. No. 08/389,437 (now allowed), Attorney Docket No. C93-007FWC, filed Feb. 15, 1995; and Automated Optical Inspection Apparatus Using Nearest Neighbor Interpolation, filed 02 May, 1994, Ser. No. 08/236,215 (now pending).

Figure 4:
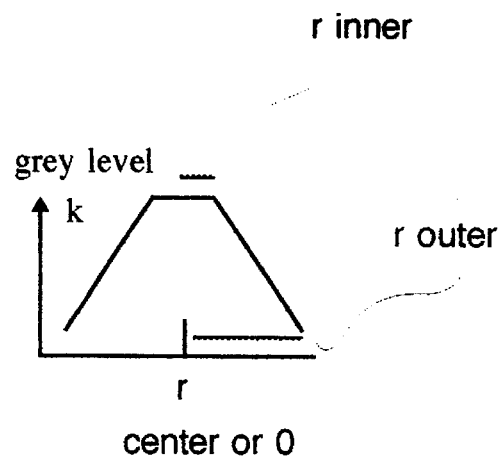
FIG. 4 is a plot of a cone shape.

Proceeding to FIG. 4, a plot or graph of a cone shape is illustrated. The axes of the graph show grey level values on the y axis, indicated here as k, and the locations of r-inner, r-outer, and a center point on the x axis, indicted here as r. The present invention uses these and other values to create a flattened synthetic cone shaped model 120, as shown in FIG. 5.

Figure 5:
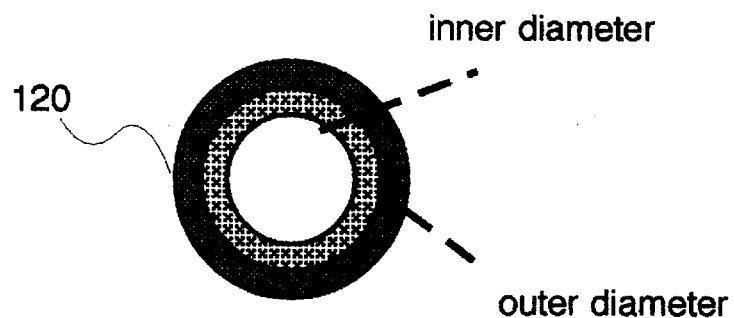
FIG. 5 is a top view of a flattened cone shaped model according to the method and apparatus of the present invention.

Here, in FIG. 5, a model is depicted containing three different grey levels. An innermost circle, having an inner diameter, is depicted here as the lightest valued. An outermost circle, having an outer diameter, is shown having a darkest value. The central circle between these two has an intermediate grey level. As will be apparent to those skilled in the art, these gray levels can be reversed if the polarity of the image to be analyzed or the system used to conduct the search requires it. It is also apparent to those skilled in the art that additional grey levels could be created, if desired. In a preferred embodiment a model contains up to 254 grey levels.

Figure 7:
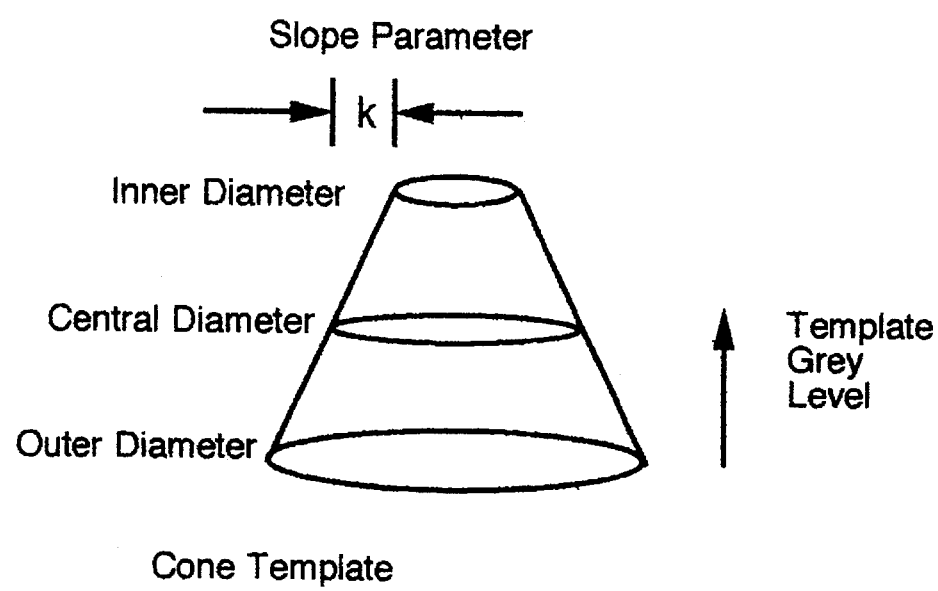
FIG. 7 is a side view of a diagram of a cone, indicating the areas of importance for generating a flattened cone-shaped model according to the method and apparatus of the present invention.

Turning to FIG. 7, the significant parameters used to create the flattened synthetic cone shaped model are illustrated in a schematic side view of a cone. A cone having an inner diameter, no smaller than the smallest expected bond size is selected by considering the maximum size circle that will be enclosed by the smallest expected bond. Similarly, a maximum outer diameter for the cone is selected by considering the minimum size circle that will enclose the largest expected bond. A number of ways to determine this will be apparent to those skilled in the art. For example, representative images of actual bonds can be created (either online or offline from the actual inspection.) These, in turn may be compared to find the smallest and largest sizes, and synthetic circles created from them. Alternatively, these can be created completely synthetically, based on known characteristics of the bonding apparatus.

Still in FIG. 7, a central diameter, between inner diameter and outer diameter is selected. The radii of these circles are used to create a monotonically increasing slope parameter k, that is a slope parameter, is created which never decreases or creates a dip or valley in the outer slope of the cone.

Referring now to FIG. 9, the overview of the creation of a flattened synthetic cone shaped model is illustrated by pseudo code. In this example, the grey level of the innermost circle is referred to as the plateau value. In the pseudocode, a value of 254, represents a very light value. NM is used for a pixel value that is not to be considered part of the model. In a preferred embodiment this is used and is called a "don't care" pixel, which is ignored by the normalized correlation search. Referring now to FIG. 9, the pseudo code, it can be seen that the flattened synthetic cone shaped model creation iterates through each pixel in the model image, starting from the top left and going from left to right across one row, then moving down to the next. In FIG. 9, the radius of a first pixel location is computed, by taking the square root of [(x-centerx)$^2$+(y-centery)$^2$]. If the radius for a pixel location is less than r inner, (in these examples, the pixels near the center of the image), then the pixel at that location is set to the plateau value. In the FIG. 9 example, the plateau value is set to 254, and the innermost pixels will have that value. Continuing with the pseudocode in FIG. 9, the grey level of the outermost circle locations are set to the grey level appropriate for that place on the slope, if it less than r outer. For the intermediate levels, grey level is set to a value calculated as slope times (r outer minus the radius (r)) at that point on the slope.

If the radius for a given pixel location is larger than r outer the value for that location is set to NM, or whatever that vision processor system uses to indicate that pixel is not in the model.

In a preferred embodiment, software code written in the C language is used to create the model, as illustrated in FIG. 10. Any of a number of variations of software embodiments of this code could be created in C or other computer languages, such as assembler.

It will be apparent to those skilled in the art that a model resembling the flattened synthetic cone shaped model generated according to the method and apparatus of the present invention could be created by arbitrarily creating a pixel model having three or more varying grey levels in concentric circles set as constants. However, a different model would have to be created for each different wirebonder or each different chip and bond size. Given the typical variations in bond sizes, arbitrary models thus constructed would be more difficult to use and manage.

Figure 6:
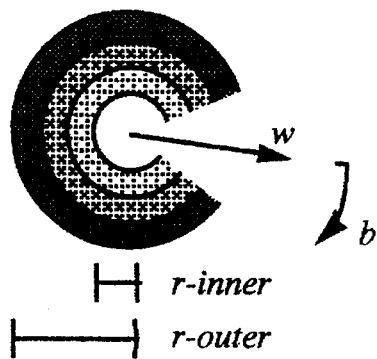
FIG. 6 is a top view of a preferred embodiment of the flattened cone shaped model of the present invention showing a wedge-shaped portion of the model which is blank.

In a preferred embodiment, creating the flattened synthetic cone shaped model according to the method and apparatus of the present invention permits the model to be modified to accommodate the confusion caused by the protrusion of the wire from the bond. In FIG. 6, such a modification is shown.

In FIG. 6 a wedge shape or pie slice around the angle of the wire is suppressed when the model is created. Specifically, if the wire angle is w, the wedge shaped area b, is created around the wire angle. In a preferred embodiment this is accomplished by inserting NM or don't care pixels for the pixels in that area.

Figure 8:
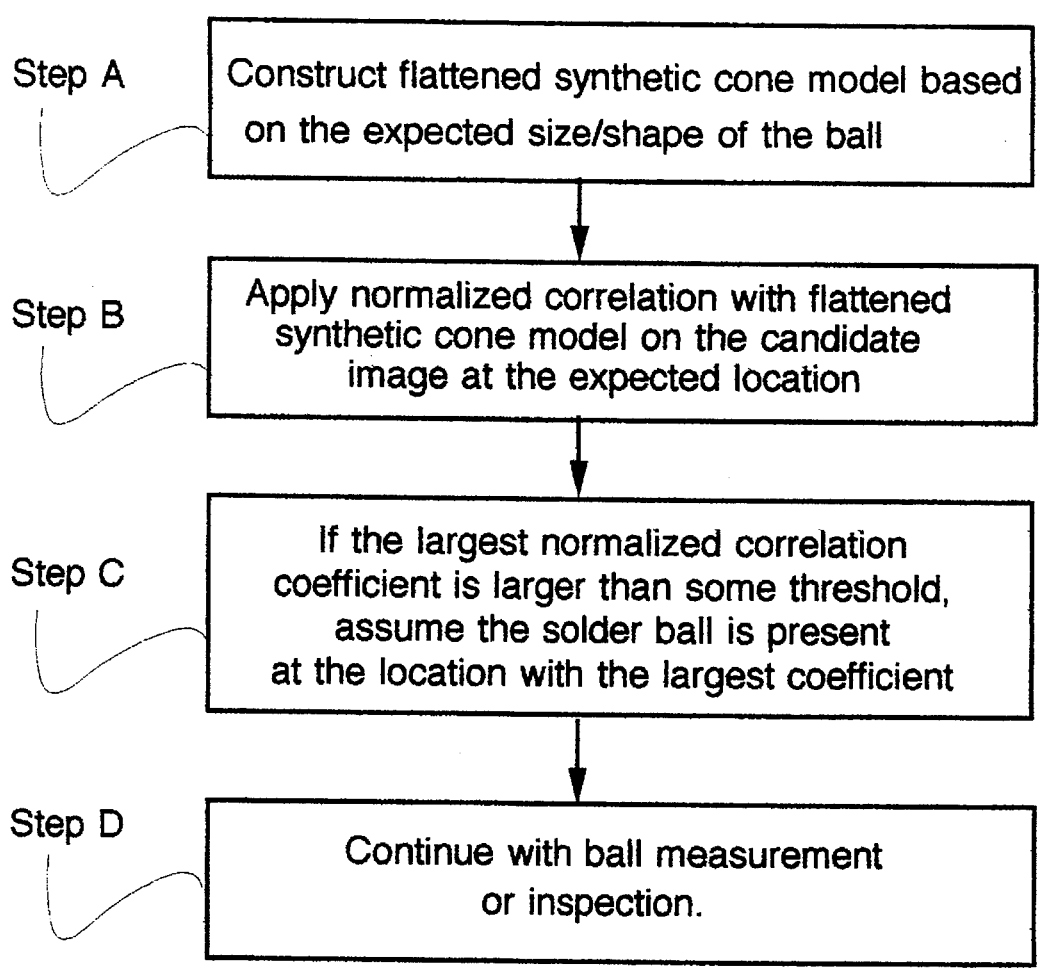
FIG. 8 is a flow diagram of the principal operations of the present invention.

Turning now to FIG. 8, it can be seen that a first step A, of the invention is the creation of the flattened synthetic cone shaped model as described above. In a preferred embodiment this is done offline, but it can also be created online during a bonding and inspection process.

In Step B of FIG. 8, the flattened synthetic cone shaped model created according to the method and apparatus of the present invention is used as the model for a normalized correlation search in the area of the image at the nominal or expected location of the bond. This step is performed at runtime or online, either in an in-process inspection embodiment or in can also be done at runtime in an offline post process inspection embodiment. As is known to those skilled in the art, normalized correlation is a measure of the geometric similarity between an image and a model, independent of any linear differences in image or model brightness. The normalized correlation value does not change in either of the following situations: if all image or model pixels are multiplied by a constant if a constant is added to all image or model pixels. This independence of normalized correlation from linear brightness changes is one of its most important attributes.

The result returned by the search is a correlation coefficient, which indicates the extent to which the image matches the model, and an x,y location in the image indicating the center of the image found to be matching. A perfect match would equal a 1, near matches would be some value less than 1, such as 0.95. In a preferred embodiment a normalized correlation search that accepts and reports on threshold values is used. For example, a user could specify that images with a correlation coefficient less than 0.50 would not be considered matches. In that case, the search would return a not found signal if all results are lower than the threshold.

In a preferred embodiment, in which the nominal location of the bond has been found before application of the flattened synthetic cone shaped model, a low threshold value is set for the normalized correlation search with the model so that not found signals are generated infrequently or not at all. The location having the largest coefficient returned by the normalized correlation search is assumed to represent the location of the solder ball, if it is above the specified threshold.

Once the solder ball has been located more precisely according to the method and apparatus of the present invention, its actual location is signaled to a next module in the vision processor or host controller, so that inspection of the ball can continue.

Those skilled in the art will appreciate that the embodiments described above are illustrative only, and that other systems in the spirit of the teachings herein fall within the scope of the invention. It will also be apparent to those skilled in the art that the present invention can be used to locate portions of objects similar to rounded bonds on a semiconductor chip, either as part of a manufacturing step, or as a post process inspection.

A preferred embodiment of the present invention also includes a camera or other device for generating a video or image signal. The video signal generated by the camera is typically converted from analog to digital by techniques well known in the art and sent to an image memory, such as a frame grabber, or similar device for storing images. A vision processor system, which includes a computer central processing chip, and input/output capabilities, is coupled to the image memory and is used to perform image processing and analysis according to the present invention. Portions of image processing and analysis are accomplished by software programs controlling the vision processor system, or, as will be evident to one skilled in the art, can be controlled by equivalent circuits created in special integrated circuit chips. The results of image processing and analysis are transmitted electronically to the apparatus or system requiring the machine vision results. Alternatively, the machine vision function can be incorporated within and work as part of a larger system.

What is claimed is:

1. An apparatus for automatically locating the center of a ball bond formed on a bonded semiconductor pad in a digitized image of said ball bond comprising:

a. means for constructing a flattened synthetic cone shaped model having a monotonically increasing slope value for concentric circles having varying grey levels, where each circle has inner and outer radii encompassing at least one expected size variation in said ball bond;

b. means for conducting a normalized correlation search in a vision processing system using said flattened synthetic cone shaped model as a search model to generate correlation coefficient signals;

c. means for evaluating said correlation coefficient signals to generate signals indicating the presence and center of said ball bond to an inspection means so that the quality of said ball bond can be inspected.

2. The apparatus of claim 1, wherein said flattened synthetic cone shaped model is created by setting pixel values in said flattened synthetic cone shaped model to a first value for pixels to be ignored by said normalized correlation search, to a second value for pixels within an outer radius (r outer) of said flattened synthetic cone shaped model corresponding to the largest expected size of said ball bond, to a third value for at least one intermediate center radius of said flattened synthetic cone shaped model and to a plateau value for the innermost radius (r inner) of said flattened synthetic cone shaped model, where the formula $$k, |r| < r \text{ inner}$$

$$\text{slope} \times (r \text{ outer} - r) \; \{|r| \geq r \text{ inner}, |r| < r \text{ outer}\}$$

$$\text{where slope} = \frac{k}{(r \text{ outer} - r \text{ inner})}$$

is used to provide a monotonically increasing slope value.

3. The apparatus of claim 1, wherein said flattened synthetic cone shaped model is created by setting pixel values in said flattened synthetic cone shaped model to a first value for pixels to be ignored by said normalized, correlation search, to a second value for pixels within an outer radius (r outer) of said flattened synthetic cone shaped model corresponding to the largest expected size of said ball bond, to a third value for at least one intermediate center radius of said flattened synthetic cone shaped model and to a plateau value for the innermost radius (r inner) of said flattened synthetic cone shaped model, where the said first value, second value, and said plateau values are predetermined constants that differ from each other.

4. The apparatus of claim 1, further comprising:
means for not defining said flattened synthetic cone shaped search model at angles plus and minus a specified number of degrees around the incident wire angle, (w) in said digitized image of said ball bond.

5. A method for automatically locating the center of a ball bond formed on a bonded semiconductor pad in a digitized image of said ball bond comprising:

a. constructing a flattened synthetic cone shaped model having a monotonically increasing slope value for concentric circles having varying grey levels, where each circle has inner and outer radii encompassing at least one expected size variation in said ball bond;

b. conducting a normalized correlation search in a vision processing system using said flattened synthetic cone shaped model as a search model to generate correlation coefficient signals;

c. evaluating said correlation coefficient signals to generate signals indicating the presence and center of said ball bond to an inspection means so that the quality of said ball bond can be inspected.

6. The method of claim 5, wherein said flattened synthetic cone shaped model is created by setting pixel values in said flattened synthetic cone shaped model to a first value for pixels to be ignored by said normalized correlation search, to a second value for pixels within an outer radius (r outer) of said flattened synthetic cone shaped model corresponding to the largest expected size of said ball bond, to a third value for at least one intermediate center radius of said flattened synthetic cone shaped model and to a plateau value for the innermost radius (r inner) of said flattened synthetic cone shaped model, where the formula $$k, |r| < r \text{ inner}$$

$$\text{slope} \times (r \text{ outer} - r) \; \{|r| \geq r \text{ inner}, |r| < r \text{ outer}\}$$

$$\text{where slope} = \frac{k}{(r \text{ outer} - r \text{ inner})}$$

is used to provide a monotonically increasing slope value.

7. The method of claim 5, wherein said flattened synthetic cone shaped model is created by setting pixel values in said flattened synthetic cone shaped model to a first value for pixels to be ignored by said normalized correlation search, to a second value for pixels within an outer radius (r outer) of said flattened synthetic cone shaped model corresponding to the largest expected size of said ball bond, to a third value for at least one intermediate center radius of said flattened synthetic cone shaped model and to a plateau value for the innermost radius (r inner) of said flattened synthetic cone shaped model, where the said first value, second value, and said plateau values are predetermined constants that differ from each other.

8. The method of claim 5, further comprising the step of: not defining said flattened synthetic cone shaped search model at angles plus and minus a specified number of degrees around the incident wire angle, (w) in said digitized image of said ball bond.

* * * * *